United States Patent
Moran

(10) Patent No.: US 10,232,008 B1
(45) Date of Patent: Mar. 19, 2019

(54) MULTI-PURPOSE NUTRITIONAL SUPPLEMENT COMPOSITION

(71) Applicant: Michael P. Moran, Naples, FL (US)

(72) Inventor: Michael P. Moran, Naples, FL (US)

(*) Notice: Subject to any disclaimer, the term of this patent is extended or adjusted under 35 U.S.C. 154(b) by 0 days.

(21) Appl. No.: 15/286,400

(22) Filed: Oct. 5, 2016

Related U.S. Application Data

(60) Provisional application No. 62/237,049, filed on Oct. 5, 2015.

(51) Int. Cl.

| | | |
|---|---|---|
| *A61K 38/01* | (2006.01) | |
| *A61K 31/375* | (2006.01) | |
| *A61K 31/07* | (2006.01) | |
| *A61K 31/355* | (2006.01) | |
| *A61K 31/593* | (2006.01) | |
| *A61K 38/16* | (2006.01) | |
| *A23L 33/185* | (2016.01) | |
| *A23L 33/155* | (2016.01) | |
| *A23L 33/175* | (2016.01) | |
| *A23L 33/17* | (2016.01) | |
| *A23L 33/15* | (2016.01) | |
| *A23L 27/30* | (2016.01) | |

(52) U.S. Cl.
CPC ............ *A61K 38/014* (2013.01); *A23L 27/36* (2016.08); *A23L 33/15* (2016.08); *A23L 33/155* (2016.08); *A23L 33/17* (2016.08); *A23L 33/175* (2016.08); *A23L 33/185* (2016.08); *A61K 31/07* (2013.01); *A61K 31/355* (2013.01); *A61K 31/375* (2013.01); *A61K 31/593* (2013.01); *A61K 38/168* (2013.01); *A23V 2002/00* (2013.01); *A23V 2250/258* (2013.01)

(58) Field of Classification Search
None
See application file for complete search history.

(56) References Cited

U.S. PATENT DOCUMENTS

| | | | |
|---|---|---|---|
| 7,205,007 B2 | 4/2007 | Lane | |
| 2011/0293813 A1* | 12/2011 | Cavallini | ............ A23C 9/1307 426/575 |
| 2014/0212565 A1* | 7/2014 | Bradley | .................... A23L 2/56 426/580 |

FOREIGN PATENT DOCUMENTS

| | | | |
|---|---|---|---|
| CN | 103349198 A | * | 10/2013 |
| JP | 63104926 A | * | 5/1988 |

OTHER PUBLICATIONS

Erdman et al., Nutrition and Traumatic Brain Injury: Improving Acute and Subacute Health Outcomes in Military Personnel, Institute of Medicine of the National Academies, 2011; chapter 8, p. 108 (Year: 2011).*

Just Vitamins ("Bovine Collagen vs Porcine Collagen", https://www.justvitamins.co.uk/blog/bovine-collagen-vs-marine-collagen/#.WkLOP195aQ; Jun. 14, 2014; accessed on Jan. 5, 2018 pp. 1-2 (Year: 2014).*

Baginski et al., Response Response to to Hydrolyzed Hydrolyzed Collagen Collagen Protein Supplementation in a Cohort of Protein Supplementation in a Cohort of Pregnant and Postpartum Patients <retrieved on Oct. 5, 2016 from: https://protivamom.com/clinical-study/>.

* cited by examiner

*Primary Examiner* — Lianko G Garyu
(74) *Attorney, Agent, or Firm* — Law Office of Sam Sokhansanj PLLC

(57) ABSTRACT

One or more multi-purpose compositions formulated for pre-operative, post-operative, pregnancy, and postpartum recovery are disclosed in liquid or solid form, having high quality protein, nutrients, minerals (calcium, iron, zinc, and copper), antioxidants, and vitamins A, C, D, and E that are non-GMO and allergen free in vegan, gluten-free, preservative-free, and lactose-free formulations. Here, the multi-purpose formulations promote fast recovery and wound healing after an invasive medical procedure, during and post pregnancy and delivery, and further prevent post-operative complications, among other advantages.

14 Claims, 9 Drawing Sheets

PRE-OP BERRY COMPOSITION

| INGREDIENT | ELEMENTAL AMOUNT | BONDED AMOUNT |
|---|---|---|
| Calcium (as Calcium Citrate Tetrahydrate)(JOST) | 500 MG | 2,500 mg |
| Copper (as Copper bisglycinate Chelate) | 1 MG | 10 mg |
| Zinc (as zinc gluconate) (Jost) | 3.75 MG | 31.25 mg |
| Flavor ( FLAVOR SWEET (A NATURAL FLAVOR) - FCI # 40018125 | 50 MG | 50 mg |
| Vitamin C (as Ascorbic Acid) | 50 MG | 50 mg |
| Rebaudioside A (DeBittereized Stevia 98%) | 30 MG | 30 mg |
| Stevia (90% Steviosides) | 40 MG | 40 mg |
| Coconut Palm Sugar (Customer supplied - OS) | 8000 MG | 8,000 mg |
| Xanthan Gum | 400 MG | 400 mg |
| Guar Gum MG250F | 200 MG | 200 mg |
| Beet Root Powder (Ecuadorian Rainforest; 5 kg pack) | 400 MG | 400 mg |
| Vitamin A (as Retinyl Palmitate) | 2500 IU | 2,500 IU |
| Flavor (Natural Strawberry Ice Cream) - FCI #83194135 (Outsource Provided) | 400 MG | 400 mg |
| Sipernat 50S | 70 MG | 70 mg |
| Flavor (Cookies & Cream N&A) - FCI #28066145 (Outsource Provided) | 100 MG | 100 mg |
| Vitamin D3 (Cholecalciferol)(on beta-cyclodextrin) | 400 IU | 400 IU |
| Agenamalt 20.271 (Maltodextrin DE 19 GMO-Free) | 1885 MG | 1,885 mg |
| Collagen Solugel 5000 (Outsource Formulations) | 14800 MG | 14,800 mg |

FIG. 1A

PRE-OP CHOCOLATE COMPOSITION

| INGREDIENT | ELEMENTAL AMOUNT | BONDED AMOUNT |
|---|---|---|
| Calcium (as Calcium Citrate Tetrahydrate)(JOST) | 500 MG | 2,500 mg |
| Copper (as Copper bisglycinate Chelate) | 1 MG | 10 mg |
| Zinc (as zinc gluconate) (Jost) | 3.75 MG | 31.25 mg |
| Flavor ( FLAVOR SWEET (A NATURAL FLAVOR) - FCI # 40018125 | 100 MG | 100 mg |
| Vitamin C (as Ascorbic Acid) | 50 MG | 50 mg |
| Rebaudioside A (DeBittereized Stevia 98%) | 35 MG | 35 mg |
| Stevia (90% Steviosides) | 50 MG | 50 mg |
| Coconut Palm Sugar (Customer supplied - OS) | 8000 MG | 8,000 mg |
| Xanthan Gum | 400 MG | 400 mg |
| Guar Gum MG250F | 200 MG | 200 mg |
| Cocoa (Dutch Processed Cocoa) | 2000 MG | 2,000 mg |
| Vitamin A (as Retinyl Palmitate) | 2500 IU | 2,500 IU |
| Flavor (Cookies & Cream N&A) - FCI #28066145 (Outsource Provided) | 500 MG | 500 mg |
| Sipernat 50S | 70 MG | 70 mg |
| Flavor (Chocolate powder Natural) FCI #240015145 - (Outsource Provided) | 600 MG | 600 mg |
| Flavor (Hazelnut N&A) - FCI#46004135 (Outsource Provided) | 100 MG | 100 mg |
| Vitamin D3 (Cholecalciferol)(on beta-cyclodextrin) | 400 IU | 400 IU |
| Agenamalt 20.271 (Maltodextrin DE 19 GMO-Free) | 1514 MG | 1,514 mg |
| Collagen Solugel 5000 (Outsource Formulations) | 14800 MG | 14,800 mg |

FIG. 1B

PRE-OP VEGAN CHOCOLATE COMPOSITION

| INGREDIENT | ELEMENTAL AMOUNT | BONDED AMOUNT |
|---|---|---|
| Calcium (as Calcium Citrate Tetrahydrate)(JOST) | 500 MG | 2,500 mg |
| Copper (as Copper bisglycinate Chelate) | 1 MG | 10 mg |
| Zinc (as zinc gluconate) (Jost) | 3.75 MG | 31.25 mg |
| Flavor ( FLAVOR SWEET (A NATURAL FLAVOR) - FCI # 40018125 | 120 MG | 120 mg |
| Vitamin C (as Ascorbic Acid) | 50 MG | 50 mg |
| Rebaudioside A (DeBittereized Stevia 98%) | 35 MG | 35 mg |
| Stevia (90% Steviosides) | 50 MG | 50 mg |
| Coconut Palm Sugar (Customer supplied - OS) | 8000 MG | 8,000 mg |
| Xanthan Gum | 450 MG | 450 mg |
| Guar Gum MG250F | 250 MG | 250 mg |
| Cocoa (Dutch Processed Cocoa) | 2000 MG | 2,000 mg |
| Vitamin A (as Retinyl Palmitate) | 2500 IU | 2,500 IU |
| Flavor (Chocolate powder Natural) FCI #240015145 - (Outsource Provided) | 300 MG | 300 mg |
| Flavor (Peanut Butter Chocolate N&A) - FCI #69005135 (Outsource Provided) | 200 MG | 200 mg |
| Flavor (Hazelnut N&A) - FCI#46004135 (Outsource Provided) | 100 MG | 100 mg |
| Vitamin D3 (Cholecalciferol)(on beta-cyclodextrin) | 400 IU | 400 IU |
| Oryzatein(R) Silk 80 Organic (Brown Rice Protein Conc.) (Outsource Prov.) | 12000 MG | 12,000 mg |
| Incatein(TM) Organic (Sachi Inchi Protein Powder) (Outsource Prov.) | 5900 MG | 5,900 mg |
| Hemp Protein 45% (seed) (Outsource Provided) | 800 MG | 800 mg |
| Agenamalt 20.271 (Maltodextrin DE 19 GMO-Free) | 662 MG | 662 mg |

FIG. 1C

POST-OP BERRY COMPOSITION

| INGREDIENT | ELEMENTAL AMOUNT | BONDED AMOUNT |
|---|---|---|
| Calcium (as Calcium Citrate Tetrahydrate)(JOST) | 500 MG | 2,500 mg |
| Copper (as Copper bisglycinate Chelate) | 1 MG | 10 mg |
| Zinc (as zinc gluconate) (Jost) | 3.75 MG | 31.25 mg |
| Flavor ( FLAVOR SWEET (A NATURAL FLAVOR) - FCI #40018125 | 50 MG | 50 mg |
| Vitamin C (as Ascorbic Acid) | 375 MG | 375 mg |
| Rebaudioside A (DeBittereized Stevia 98%) | 30 MG | 30 mg |
| Stevia (90% Steviosides) | 40 MG | 40 mg |
| Coconut Palm Sugar (Customer supplied - OS) | 8000 MG | 8,000 mg |
| Xanthan Gum | 400 MG | 400 mg |
| Guar Gum MG250F | 200 MG | 200 mg |
| Beet Root Powder (Ecuadorian Rainforest; 5 kg pack) | 400 MG | 400 mg |
| Vitamin A (as Retinyl Palmitate) | 2500 IU | 2,500 IU |
| Vitamin E (as DL-Alpha-Tocopheryl Acetate) | 15 IU | 15 IU |
| L-Isoleucine | 200 MG | 200 mg |
| L-Leucine | 50 MG | 50 mg |
| L-Valine | 50 MG | 50 mg |
| Flavor (Natural Strawberry Ice Cream) - FCI #83194135 (Outsource Provided) | 400 MG | 400 mg |
| Sipernat 50S | 70 MG | 70 mg |
| Flavor (Cookies & Cream N&A) - FCI #28066145 (Outsource Provided) | 100 MG | 100 mg |
| Vitamin D3 (Cholecalciferol)(on beta-cyclodextrin) | 400 IU | 400 IU |
| Agenamalt 20.271 (Maltodextrin DE 19 GMO-Free) | 1550 MG | 1,550 mg |
| Collagen Solugel 5000 (Outsource Formulations) | 14800 MG | 14,800 mg |

FIG. 2A

POST-OP CHOCOLATE COMPOSITION

| INGREDIENT | ELEMENTAL AMOUNT | BONDED AMOUNT |
|---|---|---|
| Calcium (as Calcium Citrate Tetrahydrate)(JOST) | 500 MG | 2,500 mg |
| Copper (as Copper bisglycinate Chelate) | 1 MG | 10 mg |
| Zinc (as zinc gluconate) (Jost) | 3.75 MG | 31.25 mg |
| Flavor ( FLAVOR SWEET (A NATURAL FLAVOR) - FCI # 40018125 | 100 MG | 100 mg |
| Vitamin C (as Ascorbic Acid) | 375 MG | 375 mg |
| Rebaudioside A (DeBittereized Stevia 98%) | 35 MG | 35 mg |
| Stevia (90% Steviosides) | 50 MG | 50 mg |
| Coconut Palm Sugar (Customer supplied - OS) | 8000 MG | 8,000 mg |
| Xanthan Gum | 400 MG | 400 mg |
| Guar Gum MG250F | 200 MG | 200 mg |
| Cocoa (Dutch Processed Cocoa) | 2000 MG | 2,000 mg |
| Vitamin A (as Retinyl Palmitate) | 2500 IU | 2,500 IU |
| Vitamin E (as DL-Alpha-Tocopheryl Acetate) | 15 IU | 15 IU |
| L-Isoleucine | 200 MG | 200 mg |
| L-Leucine | 50 MG | 50 mg |
| L-Valine | 50 MG | 50 mg |
| Sipernat 50S | 70 MG | 70 mg |
| Flavor (Chocolate powder Natural) FCI #240015145 - (Outsource Provided) | 600 MG | 600 mg |
| Flavor (Hazelnut N&A) - FCI#46004135 (Outsource Provided) | 100 MG | 100 mg |
| Flavor (Cookies & Cream N&A) - FCI #28066145 (Outsource Provided) | 500 MG | 500 mg |
| Vitamin D3 (Cholecalciferol)(on beta-cyclodextrin) | 400 IU | 400 IU |
| Agenamalt 20.271 (Maltodextrin DE 19 GMO-Free) | 1184 MG | 1,184 mg |
| Collagen Solugel 5000 (Outsource Formulations) | 14800 MG | 14,800 mg |

FIG. 2B

POST-OP VEGAN CHOCOLATE COMPOSITION

| INGREDIENT | ELEMENTAL AMOUNT | BONDED AMOUNT |
|---|---|---|
| Calcium (as Calcium Citrate Tetrahydrate)(JOST) | 500 MG | 2,500 mg |
| Copper (as Copper bisglycinate Chelate) | 1 MG | 10 mg |
| Zinc (as zinc gluconate) (Jost) | 3.75 MG | 31.25 mg |
| Flavor ( FLAVOR SWEET (A NATURAL FLAVOR) - FCI # 40018125 | 120 MG | 120 mg |
| Vitamin C (as Ascorbic Acid) | 375 MG | 375 mg |
| Rebaudioside A (DeBittereized Stevia 98%) | 35 MG | 35 mg |
| Stevia (90% Steviosides) | 50 MG | 50 mg |
| Coconut Palm Sugar (Customer supplied - OS) | 8000 MG | 8,000 mg |
| Xanthan Gum | 450 MG | 450 mg |
| Guar Gum MG250F | 250 MG | 250 mg |
| Cocoa (Dutch Processed Cocoa) | 2000 MG | 2,000 mg |
| Vitamin A (as Retinyl Palmitate) | 2500 IU | 2,500 IU |
| Vitamin E (as DL-Alpha-Tocopheryl Acetate) | 15 IU | 15 IU |
| L-Isoleucine | 200 MG | 200 mg |
| L-Leucine | 50 MG | 50 mg |
| L-Valine | 50 MG | 50 mg |
| Flavor (Chocolate powder Natural) FCI #240015145 - (Outsource Provided) | 300 MG | 300 mg |
| Flavor (Peanut Butter Chocolate N&A) - FCI #69005135 (Outsource Provided) | 200 MG | 200 mg |
| Flavor (Hazelnut N&A) - FCI#46004135 (Outsource Provided) | 100 MG | 100 mg |
| Vitamin D3 (Cholecalciferol)(on beta-cyclodextrin) | 400 IU | 400 IU |
| Incatein(TM) Organic (Sachi Inchi Protein Powder) (Outsource Prov.) | 5900 MG | 5,900 mg |
| Oryzatein(R) Silk 80 Organic (Brown Rice Protein Conc.) | 12000 MG | 12,000 mg |
| Hemp Protein 45% (seed) (Outsource Provided) | 800 MG | 800 mg |
| Agenamalt 20.271 (Maltodextrin DE 19 GMO-Free) | 1330 MG | 1,330 mg |

FIG. 2C

PREGNANCY COMPOSITION

| Active Ingredients | Label Claim - Potency | % Potency Correction | % Overage | Actual Percentage | Actual Amount (g/serving) |
|---|---|---|---|---|---|
| Hydrolyzed Pork Collagen | 15g protein - 90% Protein, as is basis | 10% | 0% | 0.5747130 | 16.6666660 |
| Evap Cane Juice Sugar | N/A - N/A | N/A | N/A | 0.1970680 | 5.7150000 |
| Calcium Citrate | 500mg Calcium - >=20% | 80% | 10% | 0.0903120 | 2.6190480 |
| Maltodextrin 150 IP | N/A - N/A | N/A | N/A | 0.0721940 | 2.0936300 |
| FLV NAT Vanilla Non-GMO | N/A - N/A | N/A | N/A | 0.0241380 | 0.7000000 |
| FLV NAT Van Non-GMO | N/A - N/A | N/A | N/A | 0.0103450 | 0.3000000 |
| Xanthan Gum | N/A - N/A | N/A | N/A | 0.0068970 | 0.2000000 |
| Potassium Citrate | N/A - N/A | N/A | N/A | 0.0064130 | 0.1859720 |
| Salt (Sodium Chloride) | N/A - N/A | N/A | N/A | 0.0044830 | 0.1300000 |
| Guar Gum G2 | N/A - N/A | N/A | N/A | 0.0034480 | 0.1000000 |
| Silicon Dioxide | N/A - N/A | N/A | N/A | 0.0034480 | 0.1000000 |
| Swevia Stevia 95% Reb A | N/A - N/A | N/A | N/A | 0.0024140 | 0.0700000 |
| Ascorbic Acid Vit C | 50mg Vitamin C - >=99% | 1% | 30% | 0.0022640 | 0.0656570 |
| Zinc Gluconate | 3.75mg Zinc - >=12% | 88.0% | 10% | 0.0011110 | 0.0322270 |
| Copper Acid Chelate 10% | 1mg Copper - >=10% | 90% | 10% | 0.0003790 | 0.0110000 |
| Vitamin A Palmitate 250 | 1250 IU Vitamin A - >=125,000 IU/g | N/A | 20% | 0.0002070 | 0.0060000 |
| Cholecalciferol Vit D3 | 400 IU Vitamin D3 - >=90,000 IU/g | N/A | 20% | 0.0001660 | 0.0048000 |
| | | | Totals: | 100% | 29.00 |

FIG. 3A

POST-PREGNANCY COMPOSITION

| Active Ingredients | Label Claim - Potency | % Potency Correction | % Overage | Actual Percentage | Actual Amount (g/serving) |
|---|---|---|---|---|---|
| Hydrolyzed Pork Collagen | 15g Protein - 90% protein, as is basis | 10% | 0% | 57.4713% | 16.6666700 |
| Evap Cane Juice Sugar | N/A | N/A | N/A | 19.7069% | 5.7150000 |
| Calcium Citrate | 500mg Calcium - >=20% | 80% | 10% | 9.0312% | 2.6190490 |
| Maltodextrin 150 IP | N/A | N/A | N/A | 3.5596% | 1.0322890 |
| FLV NAT FrenchVan Non-GMO | N/A | N/A | N/A | 2.4138% | 0.7000000 |
| Ascorbic Acid Vit C | 375mg Vitamin C - >=99% | 1% | 30% | 1.6980% | 0.4924240 |
| FLV NAT Van WONF Non-GMO | N/A | N/A | N/A | 1.0345% | 0.3000000 |
| Xanthan Gum | N/A | N/A | N/A | 0.6897% | 0.2000000 |
| Fermented L-Leucine | N/A | N/A | N/A | 0.6897% | 0.2000000 |
| L-Valine | N/A | N/A | N/A | 0.6897% | 0.2000000 |
| L-Isoleucine | N/A | N/A | N/A | 0.6897% | 0.2000000 |
| Potassium Citrate | N/A | N/A | N/A | 0.6413% | 0.1859720 |
| Salt (Sodium Chloride) | N/A | N/A | N/A | 0.4483% | 0.1300000 |
| Guar Gum G2 | N/A | N/A | N/A | 0.3448% | 0.1000000 |
| Silicon Dioxide | N/A | N/A | N/A | 0.3448% | 0.1000000 |
| Swevia Stevia 95% Reb A | N/A | N/A | N/A | 0.2414% | 0.0700000 |
| Zinc Gluconate | 3.75mg Zinc - >=12% | 87% | 10% | 0.1111% | 0.0322270 |
| d-Alpha Tocopheryl 630IU | 15 IU Vitamin E - >=630 IU/g | N/A | 20% | 0.0985% | 0.0285700 |
| Vitamin A Palmitate 250 | 2500 IU Vitamin A - >=250,000 IU/g | N/A | 20% | 0.0414% | 0.0120000 |
| Copper Acid Chelate 10% | 1mg Copper - >=10% | 90% | 10% | 0.0379% | 0.0110000 |
| Cholecalciferol Vit D3 | 400 IU Vitamin D3 - >=90,000 IU/g | N/A | 20% | 0.0166% | 0.0048000 |

Totals: 100.0000%   29

MULTI-PURPOSE NUTRITIONAL SUPPLEMENT COMPOSITION

CROSS-REFERENCE TO RELATED APPLICATION

This application claims the benefit of U.S. Provisional Application Ser. No. 62/237,049 filed on Oct. 5, 2015, which incorporated herein by reference in its entirety.

BACKGROUND

This section is intended to introduce the reader to aspects of art that may be related to various aspects of the present disclosure described herein, which are described and/or claimed below. This discussion is believed to be helpful in providing the reader with background information to facilitate a better understanding of the various aspects of the present disclosure described herein. Accordingly, it should be understood that these statements are to be read in this light, and not as admissions of prior art.

The nutritional status of patients affect the outcome of their surgical or interventional procedures, or their response to trauma. It is very common for one or more complications to occur in surgical patients during or after surgery. The overall risk for surgical complications depends on many individual factors and the type of surgical procedure, however, malnourishment or sub-optimal nourishment is an important factor in the incidence of complications. Malnourished patients experience increased morbidity and mortality when faced with the stresses of surgery, malnutrition, interventional procedures, or trauma. Further, the nutritional status of a person affects their ability to heal after a surgical procedure. After a surgical operation, the body's immune system is weakened and gastrointestinal function is often changed, leaving the body vulnerable to infection and in a state of nutritional insufficiency, thus compromising wound healing and delaying the rate of recovery. Harmful nutritional deficiency is even more likely when the person already is in a state of marginal or sub-optimal nutrition prior to the injury or procedure and when the person is unable to eat normally due to the procedure, for example after oral or gastrointestinal surgery.

Therefore, it is essential for patients to have proper nutritional supplementation in the pre-operative and post-operative period to facilitate wound healing and to expedite recovery while at the same time avoiding foods and supplements with detrimental or deleterious effects. Hence, what is needed is a pre-operative and post-operative nutritional supplement formulation, either in liquid or solid form, that can be easily administered, provides the necessary protein, nutrients, minerals, and vitamins to a patient, and that helps prevent surgical complications and promotes faster recovery and wound healing after an invasive surgical procedure.

In addition, pregnancy is associated with physiologic changes that result in increased plasma volume and red blood cells and decreased concentrations of circulating nutrient-binding proteins and micronutrients. There is an increased requirement for vitamins and minerals during pregnancy relative to the non-pregnant state. The demand for protein during the second and third trimester of pregnancy can increase up to 1.1 g/kg/day or approximately 71 g, which generally amounts to more than a 50% increase in protein that is necessary for fetal growth and maternal milk production. Many women find it difficult to consume the recommended amount of protein during and after pregnancy. Further, physicians and caregivers are often short on time and find it difficult to address the many dietary concerns and restrictions that face the gravid patient. Women looking for additional protein during pregnancy may find protein powders an easy and convenient alternative to other forms of unprocessed protein. Unfortunately there is insufficient data regarding the impact on these drinks on either the mother or the fetus to routinely recommend them during pregnancy. Hence, what is needed is a nutritional supplement formulation, either in liquid or solid form, that can provide the adequate amount of protein needed by women during pregnancy and after pregnancy, that can assist with labor during pregnancy and further promote faster recovery after child birth.

BRIEF SUMMARY

In one aspect of the disclosure described herein, a multi-purpose nutritional supplement formulation having pre-operative, post-operative (recovery) formulations are disclosed in liquid or solid form, having collagen protein, nutrients, minerals (calcium, iron, zinc, and copper), antioxidants, and vitamins A, C, D, and E that is non-GMO and allergen free in vegan, gluten-free, preservative-free, and lactose-free formulations, thereby promoting fast recovery and wound healing after an invasive medical procedure and further preventing post-operative complications.

In another aspect of the disclosure described herein, a multi-purpose nutritional supplement formulation having pregnancy and post-pregnancy formulations are disclosed in liquid or solid form, having collagen protein, nutrients, minerals (calcium, iron, zinc, and copper), antioxidants, and vitamins A, C, D, and E that is non-GMO and allergen free in vegan, gluten-free, preservative-free, and lactose-free formulations, thereby improving labor, the health of a newborn, and promoting fast recovery and wound healing.

In another aspect of the disclosure described herein, a nutritional protein supplement formulation is disclosing having hydrolyzed collagen protein, Rebaudioside-A or Reb-A, vitamin C, and a flavoring ingredient. Further, the hydrolyzed collagen protein is comprised of at least 50% wt. of the formulation. In addition, the hydrolyzed collagen protein may comprise at least approximately 15 grams of the formulation. Alternatively, the hydrolyzed collagen protein may comprise at least 5 grams of the formulation. Further, the hydrolyzed collagen protein is comprises from 14 grams up to and including 16 grams of the formulation. Here, the hydrolyzed collagen protein is can include bovine or porcelain animal protein sources. In addition, the formulation can also include L-Isoleucine, L-Leucine, and L-Valine. Also, the formulation may include vitamin A, vitamin E, and vitamin D3.

In another aspect of the disclosure described herein, a nutritional protein supplement formulation is disclosed having hydrolyzed collagen protein, Rebaudioside-A or Reb-A, vitamin C, a flavoring ingredient, L-Isoleucine, L-Leucine, and L-Valine. In addition, the hydrolyzed collagen protein can include at least 50% wt. of the formulation. Further, the hydrolyzed collagen protein can include approximately 15 grams of the formulation.

In another aspect of the disclosure described herein, a nutritional protein supplement formulation is disclosed having brown rice protein, sacha inchi protein, hemp protein, Rebaudioside-A or Reb-A, and a flavoring ingredient. In addition, the formulation can include vitamin C, vitamin A, and vitamin D3. Further, the formulation can include coconut palm sugar. Here, the brown rice can include approximately 5000 to 20000 mg of the formulation, the sacha inchi protein comprises 1000 to 10000 mg of the formulation, and the hemp protein comprises 100 to 5000 mg of the formulation. In addition, the brown rice can include approximately 12 grams of the formulation, the sacha inchi protein can include approximately 6 grams of the formulation, and the hemp protein can include approximately 0.8 grams of the formulation.

The above summary is not intended to describe each and every disclosed embodiment or every implementation of the disclosure. The Description that follows more particularly exemplifies the various illustrative embodiments.

BRIEF DESCRIPTION OF THE DRAWINGS

The following description should be read with reference to the drawings, in which like elements in different drawings are numbered in like fashion. The drawings, which are not necessarily to scale, depict selected embodiments and are not intended to limit the scope of the disclosure. The disclosure may be more completely understood in consideration of the following detailed description of various embodiments in connection with the accompanying drawings, in which:

FIG. 1A illustrates a table of ingredients for one non-limiting embodiment of a pre-operation berry composition flavor of the disclosure described herein.

FIG. 1B illustrates a table of ingredients for one non-limiting embodiment of a pre-operation chocolate composition flavor of the disclosure described herein.

FIG. 1C illustrates a table of ingredients for one non-limiting embodiment of a pre-operation vegan chocolate composition flavor of the disclosure described herein.

FIG. 2A illustrates a table of ingredients for one non-limiting embodiment of a post-operation berry composition flavor of the disclosure described herein.

FIG. 2B illustrates a table of ingredients for one non-limiting embodiment of a post-operation chocolate composition flavor of the disclosure described herein.

FIG. 2C illustrates a table of ingredients for one non-limiting embodiment of a post-operation vegan chocolate composition flavor of the disclosure described herein.

FIG. 3A illustrates a table of ingredients for one non-limiting embodiment of a pregnancy composition of the disclosure described herein.

FIG. 3B illustrates a table of ingredients for one non-limiting embodiment of a post-pregnancy composition of the present disclosure described herein.

DETAILED DESCRIPTION

Figure 4A:
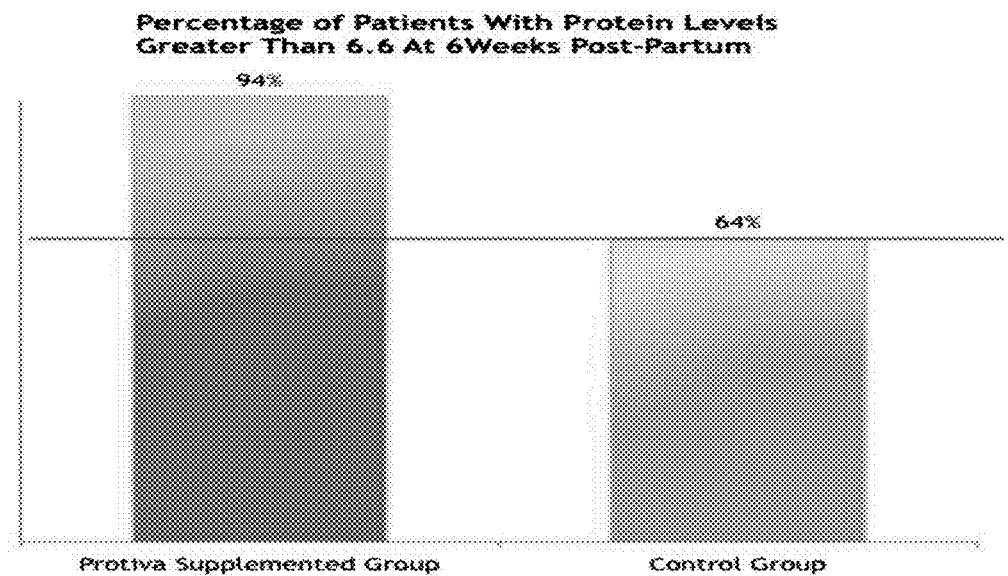
FIGS. 4A-4B illustrates bar graphs for one clinical study of the disclosure described herein.

In the Brief Summary of the present disclosure above and in the Detailed Description of the disclosure described herein, and the claims below, and in the accompanying drawings, reference is made to particular features (including method steps) of the disclosure described herein. It is to be understood that the disclosure of the disclosure described herein in this specification includes all possible combinations of such particular features. For example, where a particular feature is disclosed in the context of a particular aspect or embodiment of the disclosure described herein, or a particular claim, that feature can also be used, to the extent possible, in combination with and/or in the context of other particular aspects and embodiments of the disclosure described herein, and in the disclosure described herein generally.

The embodiments set forth below represent the necessary information to enable those skilled in the art to practice the disclosure described herein and illustrate the best mode of practicing the disclosure described herein. In addition, the disclosure described herein does not require that all the advantageous features and all the advantages need to be incorporated into every embodiment of the disclosure described herein.

Here, the pre-op, post-op, pregnancy, and post-pregnancy formulations of the disclosure described herein may also be referred to herein as ELEVATE™ or PROTIVA™ formulations.

FIGS. 1A-1C illustrate tables of ingredients for one or more non-limiting embodiments for pre-operation ("pre-op") formulations or compositions for one serving to be administered to or by a user prior to an invasive or non-invasive surgical operation or medical procedure. FIGS. 2A-2C illustrate tables of ingredients for one or more non-limiting embodiments for post-operative ("post-op") formulations or compositions to be administered to or by a user after an invasive or non-invasive surgical operation or medical procedure. FIGS. 3A-3B illustrate tables of ingredients for one or more non-limiting embodiments for a formulations to be taken during pregnancy and after pregnancy (after child birth or post-partum). However, any of the formulations within FIGS. 1A-3B may be interchangeable for their intended purpose. For example, the formulations within FIGS. 1A-2B may also be used for pregnancy or after pregnancy purposes. Alternatively, the formulations of FIGS. 3A-3B may also be used for pre-op or post-op recovery purposes. Here, it is contemplated within the scope of the disclosure described herein that the pre-op, post-up, pregnancy, and post-pregnancy formulations can be administered in any manner, such as oral drinkable administration, oral buccal administration, sub labial administration, or sublingual administration, preferably oral liquid drinkable administration. Further, the pre-op and post op formulations can be provided in powder, granules, drops, sprays, injectable, liquid, gel, pill, tablet, or capsule form, preferably in powder or liquid form. For example, in one embodiment, a serving of either one of the pre-op, post-op, pregnancy, and post-pregnancy compositions, such as one of FIGS. 1A-3B, may include mixing one scoop serving of powder form (31 g) of the compositions with 8-10 ounces of cold water, milk, or liquid of choice, taken twice a day prior to and after a surgical procedure, or during or after pregnancy.

Still referring to FIGS. 1A-3B, the formulations of the disclosure described herein can be provided in both animal based protein blend and plant based protein blend (vegan formulations). More specifically, the animal based protein formulations can include collagen (hydrolyzed gelatin protein) as shown in the embodiments of FIGS. 1A-1B, 2A-2B, 3A-3B in bovine (i.e. beef) or porcelein (i.e. pork) form, and the plant based (non-animal) formulations can include a blend of hemp, sachi inchi, and brown rice protein, among others. In particular, both the pre-op and post-op formulations of FIGS. 1A-1B and 2A-2B include 14,800 mg (elemental and bonded), approximately 15 grams, of collagen Solugel® 5000 protein (hydrolyzed gelatin protein or hydrolyzed pork collagen) having a full amino acid spectrum. Further, FIGS. 3A-3B also include In addition, the formulations of FIGS. 2A-2C include collagen Solugel® 5000 protein (hydrolyzed gelatin protein or hydrolyzed pork collagen) in approximately 16,667 mg and having a full amino acid spectrum. Here, elemental or bonded weights for any of the ingredients disclosed with respect to FIGS. 1A-3B may also be represented as percent weight, percentage by weight, % wt., or wt %. It is contemplated within the scope of the disclosure described herein that any of the formulations having the hydrolyzed pork collagen may have amounts ranging from 100 mg up to and including 100,000 mg of collagen protein, hydrolyzed pork collagen, or beef collagen. Further, additional amino acids such as L-Isoleucine at 200 mg (elemental and bonded), L-Leucine at 50 mg (elemental and bonded), and L-Valine at 50 mg (elemental and bonded), FIG. 3B include L-Valine (200 mg) and L-Isoleucine at 200 mg, thereby further enhancing the amino acid content of the compositions. Here, both the vegan pre-op and vegan post-op compositions of FIGS. 1C and 2C include hemp (seed) protein 45% at 800 mg (elemental and bonded), Incatein™ organic sachi inchi protein powder at 5,900 mg (elemental and bonded), and Oryzatein® silk 80 organic brown rice protein concentrate at 12,000 mg (elemental and bonded). However, it is contemplated within the scope of the disclosure described herein that the protein content of either of the formulations of FIGS. 1A-2C of the disclosure described herein may be from 1 gram up to and including 100 grams per serving. In addition, the protein content of either for the formulations of FIGS. 1A-2C may include whey, casein, dairy, egg, or other animal or plant-based sources.

Still referring to FIGS. 1A-2C, the pre-op and post-op formulations of the disclosure described herein can include various amounts of vitamins A, C, D, and E. In particular, vitamin C has been shown to support wound healing, promote the formation of new connective tissue, and reduce oxidative stress. Vitamin A has been shown to promote epithelial and bone formation and growth, cellular differentiation, immune function, and in particular, helps the skin and mucous membranes repel bacteria and viruses. Vitamin D has been shown to regulate calcium and phosphorous absorption, promote creation of an antimicrobial peptide called cathelicidin, and further maintaining healthy bones and promoting bone formation. Vitamin E is most widely known to further promote a healthy immune system and protect against various neurological diseases. Here, the pre-op formulations of FIGS. 1A-1C include vitamin C as ascorbic acid at approximately 50 mg (elemental and bonded), vitamin A as retinyl palmitate at approximately 2500 IU (elemental and bonded), and vitamin D3 as cholecaliferol (on beta-cyclodexterin) at approximately 400 IU. The post-op formulations of FIGS. 2A-2C include C as ascorbic acid at approximately 375 mg (elemental and bonded), vitamin A as retinyl palmitate at approximately 2500 IU (elemental and bonded), vitamin D3 as cholecaliferol (on beta-cyclodexterin) at approximately 400 IU, and vitamin E as DL-alpha-tocopheryl acetate at approximately 15 IU. However, it is contemplated within the scope of the disclosure described herein that either of the formulations of FIGS. 1A-2C of the disclosure described herein may include vitamin C from 10 IU up to and include 20,000, vitamin A from 10 IU up to 200,000 IU, vitamin D or D3 from 10 IU up to 50,000 IU, and vitamin E from 1 IU up to 10,000 IU per serving.

Still referring to FIGS. 1A-2C, the pre-op and post-compositions of the disclosure described herein can include various minerals such as calcium, zinc, iron, and copper. Calcium is widely known to promote normal homeostatis of mammalian skin and serves as a modulator in kerinocyte proliferation and differentiation, in addition to promoting healthy bone, hearth, muscle, and nerve function. Adequate zinc supplemental is further widely known to promote proper wound healing. Copper is widely known to promote the formation of collage, increase the absorption of iron, facilitate angiogenesis, and induce vascular endolethial growth factor, among others benefits. Here, the pre-op formulations of FIGS. 1A-1C include calcium as calcium citrate tetrahydrate at approximately 500 mg (elemental) and 2,500 mg (bonded), copper as copper bisglycinate chelate at approximately 1 mg (elemental) and 10 mg (bonded), zinc as zinc gluconate at approximately 3.75 mg (elemental) and 31.25 mg (bonded). The post-op formulations of FIGS. 2A-2C include calcium as calcium citrate tetrahydrate at approximately 500 mg (elemental) and 2,500 mg (bonded), copper as copper bisglycinate chelate at approximately 1 mg (elemental) and 10 mg (bonded), zinc as zinc gluconate at approximately 3.75 mg (elemental) and 31.25 mg (bonded). However, it is contemplated within the scope of the disclosure described herein that either of the formulations of FIGS. 1A-2C of the disclosure described herein may include calcium from 100 mg up to and include 20,000 mg per serving, copper from 1 mg up to 100 mg, and zinc from 1 mg up to 100 mg per serving.

Referring now to FIG. 1A, the ingredients specific to the pre-op berry flavor formulation can include a natural flavor FCI at approximately 50 mg (elemental and bonded), Rebaudioside A (debitterized *stevia* 98%) at 30 mg (elemental and bonded), *stevia* (90% steviosides) at approximately 40 mg (elemental and bonded), coconut palm sugar at approximately 8,000 mg, xanthan gum at approximately 400 mg (elemental and bonded), guar gum MG250F at approximately 200 mg (elemental and bonded), beet root powder (Ecuadorian rainforest, 5 kg pack) at approximately 400 mg (elemental and bonded), natural strawberry ice cream flavor at approximately 400 mg (elemental and bonded), Sipernat 50S silica at approximately 70 mg (elemental and bonded), cookies and cream flavor at approximately 100 mg (elemental and bonded), and Agenamalt 20.271 maltodextrin DE GMO-free at approximately 1,885 mg (elemental and bonded). However, it is contemplated within the scope of the disclosure described herein that the composition of FIG. 1A may include any ingredient, either in addition, in combination, or in lieu of other ingredients disclosed herein and at any concentration or amount (elemental or bonded) per serving.

Referring now to FIG. 1B, the ingredients specific to the pre-op chocolate flavor formulation can include a natural flavor FCI at approximately 100 mg (elemental and bonded), Rebaudioside A (debitterized *stevia* 98%) at 35 mg (elemental and bonded), *stevia* (90% steviosides) at approximately 50 mg (elemental and bonded), coconut palm sugar at approximately 8,000 mg, xanthan gum at approximately 400 mg (elemental and bonded), guar gum MG250F at approximately 200 mg (elemental and bonded), cocoa (Dutch processed cocoa) at approximately 2,000 mg (elemental and bonded), Sipernat 50S silica at approximately 70 mg (elemental and bonded), natural chocolate flavor at approximately 600 mg (elemental and bonded), cookies and cream flavor at approximately 500 mg, hazelnut flavor at approximately 100 mg, and Agenamalt 20.271 maltodextrin DE 19 GMO-free at approximately 1,514 mg (elemental and bonded). However, it is contemplated within the scope of the disclosure described herein that the composition of FIG. 1B may include any ingredient, either in addition, in combination, or in lieu of other ingredients disclosed herein and at any concentration or amount (elemental or bonded) per serving.

Referring now to FIG. 1C, the ingredients specific to the pre-op vegan (plant-based) chocolate flavor formulation can include a natural flavor FCI at approximately 120 mg (elemental and bonded), Rebaudioside A (debitterized *stevia*

98%) at 35 mg (elemental and bonded), *stevia* (90% steviosides) at approximately 50 mg (elemental and bonded), coconut palm sugar at approximately 8,000 mg, xanthan gum at approximately 450 mg (elemental and bonded), guar gum MG250F at approximately 250 mg (elemental and bonded), cocoa (Dutch processed cocoa) at approximately 2,000 mg (elemental and bonded), natural chocolate flavor at approximately 200 mg (elemental and bonded), peanut butter flavor at approximately 500 mg, hazelnut flavor at approximately 100 mg, and Agenamalt 20.271 maltodextrin DE 19 GMO-free at approximately 662 mg (elemental and bonded). However, it is contemplated within the scope of the disclosure described herein that the composition of FIG. 1C may include any ingredient, either in addition, in combination, or in lieu of other ingredients disclosed herein and at any concentration or amount (elemental or bonded) per serving.

Referring now to FIG. 2A, the ingredients specific to the post-op berry flavor formulation can include a natural flavor FCI at approximately 50 mg (elemental and bonded), Rebaudioside A (debitterized *stevia* 98%) at 30 mg (elemental and bonded), *stevia* (90% steviosides) at approximately 40 mg (elemental and bonded), coconut palm sugar at approximately 8,000 mg, xanthan gum at approximately 400 mg (elemental and bonded), guar gum MG250F at approximately 200 mg (elemental and bonded), beet root powder (Ecuadorian rainforest, 5 kg pack) at approximately 400 mg (elemental and bonded), natural strawberry ice cream flavor at approximately 400 mg (elemental and bonded), Sipernat 50S silica at approximately 70 mg (elemental and bonded), cookies and cream flavor at approximately 100 mg (elemental and bonded), and Agenamalt 20.271 maltodextrin DE GMO-free at approximately 1,550 mg (elemental and bonded). However, it is contemplated within the scope of the disclosure described herein that the composition of FIG. 2A may include any ingredient, either in addition, in combination, or in lieu of other ingredients disclosed herein and at any concentration or amount (elemental or bonded) per serving.

Referring now to FIG. 2B, the ingredients specific to the post-op chocolate flavor formulation can include a natural flavor FCI at approximately 100 mg (elemental and bonded), Rebaudioside A (debitterized *stevia* 98%) at 35 mg (elemental and bonded), *stevia* (90% steviosides) at approximately 50 mg (elemental and bonded), coconut palm sugar at approximately 8,000 mg, xanthan gum at approximately 400 mg (elemental and bonded), guar gum MG250F at approximately 200 mg (elemental and bonded), cocoa (Dutch processed cocoa) at approximately 2,000 mg (elemental and bonded), Sipernat 50S silica at approximately 70 mg (elemental and bonded), natural chocolate flavor at approximately 600 mg (elemental and bonded), cookies and cream flavor at approximately 500 mg, hazelnut flavor at approximately 100 mg, and Agenamalt 20.271 maltodextrin DE 19 GMO-free at approximately 1,184 mg (elemental and bonded). However, it is contemplated within the scope of the disclosure described herein that the composition of FIG. 2B may include any ingredient, either in addition, in combination, or in lieu of other ingredients disclosed herein and at any concentration or amount (elemental or bonded) per serving.

Referring now to FIG. 2C, the ingredients specific to the post-op vegan (plant-based) chocolate flavor formulation can include a natural flavor FCI at approximately 120 mg (elemental and bonded), Rebaudioside A (debitterized *stevia* 98%) at 35 mg (elemental and bonded), *stevia* (90% steviosides) at approximately 50 mg (elemental and bonded), coconut palm sugar at approximately 8,000 mg, xanthan gum at approximately 450 mg (elemental and bonded), guar gum MG250F at approximately 250 mg (elemental and bonded), cocoa (Dutch processed cocoa) at approximately 2,000 mg (elemental and bonded), natural chocolate flavor at approximately 300 mg (elemental and bonded), peanut butter flavor at approximately 200 mg, hazelnut flavor at approximately 100 mg, and Agenamalt 20.271 maltodextrin DE 19 GMO-free at approximately 1,330 mg (elemental and bonded). However, it is contemplated within the scope of the disclosure described herein that the composition of FIG. 2C may include any ingredient, either in addition, in combination, or in lieu of other ingredients disclosed herein and at any concentration or amount (elemental or bonded) per serving.

In one embodiment of the disclosure described herein, one or more formulations, which may also be referred to as PROTIVA™ formulations, are disclosed having hydrolyzed collagen as a protein source, to be administered to women during pregnancy and after child birth. Here, hydrolyzed collagen is chosen for the formulations of the disclosure described herein because animal studies have demonstrated that high levels of certain amino acids were associated with reduced litter size and the health of offspring. Among these amino acids that were studied, Tryptophan was found to have the greatest negative impact on fetal development. Here, the collagen protein of the disclosure described herein contains no Tryptophan and has the lowest concentration of other detrimental amino acids in comparison to other protein sources. Hydrolyzed collagen is also easily digested and absorbed because of the low molecular weight of the peptides produced during hydrolysis. Generally, adequate protein is a requirement for proper wound healing from collagen synthesis, angiogenesis, fibroblast proliferation and maintenance of tissue oncotic pressure.

Referring to FIG. 3B, the ingredients specific to post-pregnancy can be a total serving size comprised of approximately 29 grams including hydrolyzed pork collage (also known as Solugel® 5000 protein) that is approximately 15 g of 90% protein, and more specifically approximately 16,667 or about 57% wt., or evap cane juice sugar at approximately 5,715 mg or about 19.7% wt., calcium citrate at approximately 2,619 mg or about 9% wt., Maltodextrin 150 IP at approximately 2,093 mg or about 7% wt., FLV NAT Vanilla Non-GMO flavor at approximately 700 mg or about 2% wt., FLV NAT VAN Non-GMO flavor at approximately 300 mg or about 1% wt., Xantham Gum having 200 mg or about 0.6% wt., Potassium Citrate at approximately 186 mg or about 0.6% wt., Sodium Chloride having at 130 mg or about 0.4% wt., Guar Gum G2 at approximately 100 mg or about 0.3% wt., Silicone Dioxide at approximately 100 mg or 0.3% wt., *Stevia* 95% Reb-A at approximately 70 mg or about 0.2%, Ascorbic Acid Vitamin C at approximately 65 mg or about 0.2%, Zinc Gluconate at approximately 32 mg or about 0.1% wt., Copper Acid Chelate 10% at approximately 11 mg or about 0.03% wt., Vitamin A palmitate 250 at approximately 6 mg or about 0.02% wt., and Cholecalciferol Vitamin D3 at approximately 4.8 mg or about 0.01% wt. However, it is contemplated within the scope of the disclosure described herein that the formulation may include any one or more ingredients in addition to or in lieu of the aforementioned ingredients. Further, any of the percentage weight of any of the ingredients per serving may also be modified. For example, in other embodiments the hydrolyzed pork collagen protein may range anywhere from 100 mg up to and including 100,000 mg, or from 0.1% wt. up to and including 95% wt. of the formulation.

Referring to FIG. 3A, the ingredients specific to pregnancy (or to be taken during pregnancy) can be a total serving size comprised of approximately 29 grams including hydrolyzed pork collage (also known as Solugel® 5000 protein) that is approximately 15 g of 90% protein, and more specifically approximately 16,667 or about 57% wt., evap cane juice sugar at approximately 5,715 mg or about 19.7% wt., Calcium Citrate at approximately 2,619 mg or about 9% wt., Maltodextrin 150 IP at approximately 1,032 mg or about 3.5% wt., FLV NAT French Vanilla Non-GMO flavor at approximately 700 mg or about 2.4% wt., Ascorbic Acid Vitamin C at approximately 492 mg or about 1.7% wt., FLV NAT Van WONF Non-GMO flavor at approximately 300 mg or about 1% wt., Xanthan Gum at approximately 200 mg or about 0.68% wt., Fermented L-Leucine at approximately 200 mg or about 0.68% wt., L-Valine at approximately 200 mg or 0.68% wt., L-Isoleucine at approximately 200 mg or approximately 0.68% wt., potassium citrate at approximately 186 mg or 0.64% wt., salt sodium chloride at approximately 130 mg or about 0.45% wt., guar gum G2 at approximately 100 mg or about 0.34% wt., silicone dioxide at approximately 100 mg or about 0.34% wt., Stevia 95% Reb-A at approximately 700 mg or about 0.24% wt., zinc gluconate at approximately 322 mg or about 0.11% wt., d-Alpha Tocopheryl 630 IU at approximately 285 mg or about 0.098% wt., Vitamin A palmitate 250 at approximately 120 mg or about 0.04% wt., copper acid chelate 10% at approximately 110 mg or about 0.03% wt., Cholecalciferol Vitamin D3 at approximately 40 mg or about 0.01% wt. Further, any of the percentage weight of any of the ingredients per serving may also be modified. For example, in other embodiments the hydrolyzed pork collage protein may range anywhere from 100 mg up to and including 100,000 mg, or from 0.1% wt. up to and including 95% wt. of the formulation.

At least one clinical study for one or more of the formulations of the disclosure described herein was conducted to: 1) determine the blood protein levels in a group of women in their third trimester who were well nourished with access to both adequate macro and micronutrients; 2) Provide supplementation of protein with vitamins and minerals during pregnancy, delivery and into the post partum period; 3) Evaluate the potential outcome differences of patients taking supplemental protein and vitamins and minerals compared to a control group; and 4) To see if there were any negative effects of collagen protein on fetal or maternal outcomes. In the study, female subjects between 18 and 50 years of age in their final trimester of pregnancy were considered eligible to participate after evaluation of the inclusion/exclusion criteria and completion of screening procedures. Further, The materials utilized in this study included PROTIVA™ Pregnancy and PROTIVA™ New Mom (or post-pregnancy) formulations of the disclosure described herein. Study patients were instructed to mix PROTIVA™ Pregnancy and PROTIVA™ New Mom (or post pregnancy) formulations with 8-10 oz of cold water in a blender or shaker bottle and to avoid mixing them with milk or other protein containing products. Here, PROTIVA™ Pregnancy was formulated for pregnant women to provide about 15 grams of Hydrolyzed Collagen protein per serving. PROTIVA™ Pregnancy contains no artificial colors or flavors, and is gluten, lactose, soy and preservative free. One scoop provides 25% of the RDA of Vitamin A, 80% of Vitamin C, 100% of Vitamin D, 50% of Calcium, 30% of Zinc and 50% of Copper. Further, Protiva New Mom (or post-partum or post-pregnancy) has been specifically formulated for women following delivery and while breastfeeding and contains about 15 grams of hydrolyzed collagen protein per serving. PROTIVA™ New Mom also contains no artificial colors or flavors, and is gluten, lactose, soy and preservative free. It provides 50% of the RDA of Vitamin A, 625% of Vitamin C, 100% of Vitamin D 50% of Vitamin E, 50% of Calcium, 30% of Zinc and 50% of Copper. It also contains the additional amino acids L-Leucine, L-Isoleucine and L-Valine.

Still referring to the study, were screened at two investigative sites in the United States. Screening assessments were conducted, and if patients were accepted into the study, study participants received PROTIVA™ Pregnancy mailed to their homes. Screening procedures included: medical and surgical history including medication history, review of inclusion/exclusion criteria, physical examination (including height, weight, and BMI), vital signs (BP and HR). For patients who were selected into the study, laboratory tests (chemistry and hematology) were taken and the World Health Organization Quality of Life (WHOQOL)-BREF was ad-ministered and completed prior to starting on the product. Subjects returned to the site at 6 weeks post-delivery (Visit 2) and 10 weeks post-delivery (Visit 3). The following assessments were performed during those visits: physical examination (including height, weight, and BMI), vital signs (BP and HR), review of adverse events (AEs) and concomitant medications, laboratory tests (chemistry and hematology), Patient Global Satisfaction with Treatment Scale (only completed for treatment group), WHOQOL-BREF, REEDA Scale (only for subjects that had an incision or laceration with or without repair at delivery), and PROTIVA™ Pregnancy and PROTIVA™ New Mom accountability/compliance assessment for the treatment group.

Further, this open-label study was designed to assess the efficacy and safety of: 1) PROTIVA™ Pregnancy during the third trimester of pregnancy and 2) PROTIVA™ New Mom during the first 10 weeks following delivery. The duration of this study was 14 weeks. Study patients were instructed to consume PROTIVA™ Pregnancy twice daily (30 g) in their third trimester of pregnancy until delivery and then switch to PROTIVA™ New Mom twice daily until their 10 week postpartum visit. A control group of 27 subjects were included in the study that did not receive either of the PROTIVA™ products. Clinical outcomes such as blood protein levels, complication rates, and change in body mass index (BMI) were measured. The clinical study statistically evaluated the improvement in blood protein levels of study subjects from screening to the end of study. Blood protein levels were drawn on patients between weeks 30-32 of pregnancy.

Further, statistical analyses were performed based on the treatment received by the study subject. Primary and secondary endpoints are presented by treatment received. The last observation carried forward (LOCF) method was used for missing data in the primary analysis. Statistical analysis of the study results included a Full Analysis Set (FAS) as all subjects in the treatment group who received both PROTIVA™ Pregnancy and PROTIVA™ New Mom had completed at least one post-delivery assessment; and all subjects in the control group who completed at least one post-delivery assessment were included in the FAS. The protocol was reviewed by independent Institutional Review Board (IRB). Prior to the initiation of the clinical trial, the Principal Investigators obtained written and dated approval by the IRB for the protocol and the informed consent form. The study was conducted in compliance with IRB, informed consent regulations, and International Conference on Harmonization (ICH) Good Clinical Practice (GCP). The Principal Investigator was responsible for performing the study in accordance with the protocol and GCP/ICH guidelines and for collecting, recording, and reporting the data accurately and properly. Prior to enrollment in the study, an IRB approved written informed consent was obtained from each subject.

With respect to the results of the study, the safety and efficacy analysis was conducted on 142 subjects enrolled into the study. Of the 142 subjects, 109 completed the study (i.e., returned for Visit 3), 6 subjects were lost to follow-up between Visits 1 and 3, 17 subjects demonstrated noncompliance or lack of cooperation, and 10 subjects had other reasons for discontinuation such as moving out of the area. One hundred and forty two (n=142) subjects were enrolled in the trial, all were female, 132 (93%) were Caucasian, and their mean age +−SD [min, max] was 31.5+−5.11 [19, 44] years. A total of 115 subjects were assigned to PROTIVA™ treatment and 27 to no treatment at 2 centers, and 113 (91 PROTIVA™ and 22 controls) completed the primary endpoint evaluations at least at one of the post-delivery visits 2 or 3. Efficacy analysis results were obtained from a total of 113 (91 PROTIVA™ and 22 controls) who completed the primary endpoint evaluations in at least one of the post-delivery visits 2 or 3. For the endpoint of total blood protein, based on treatment or no treatment, efficacy analysis for the total blood protein, was based on the difference in blood protein levels of the PROTIVA™ group and the Control group from Screening (Visit 1) to End of Study (Visit 3). The primary endpoint was analyzed and the change from baseline values was used for the lab chemistry endpoints. If a subject withdrew from the study without undergoing the early termination assessments, the data available up until that time was used for analysis. Missing values were imputed using LOCF imputation method.

Further, the differences between mean score for the physical health domain of WHOQOL-BREF scale in the PROTIVA™ group and the control group was statistically significant at the End of Study i.e. visit 3 (P=0.0003 for FAS population, and p=0.0001 for PPS population), meaning significant improvement in the physical health of subjects in the PROTIVA™ group compared to the control group. The mean score of all four domains increased from screening to visit 3 in the PROTIVA™ group meaning improvement in quality of life, while the mean score of all four domains decreased from screening to visit 3 in the control group. The number of responders of PGS scores for each of the two post-delivery visits clearly shows much higher percentages of subjects with a satisfaction rating of very satisfied (Visit 2: 46.1% vs 7.4%; Visit 3: 42.6% vs 3.7%) and satisfied (Visit 2: 22.6% vs 0; Visit 3: 19.1% vs 0) in the PROTIVA™ group compared to the Control group.

Figure 4B:
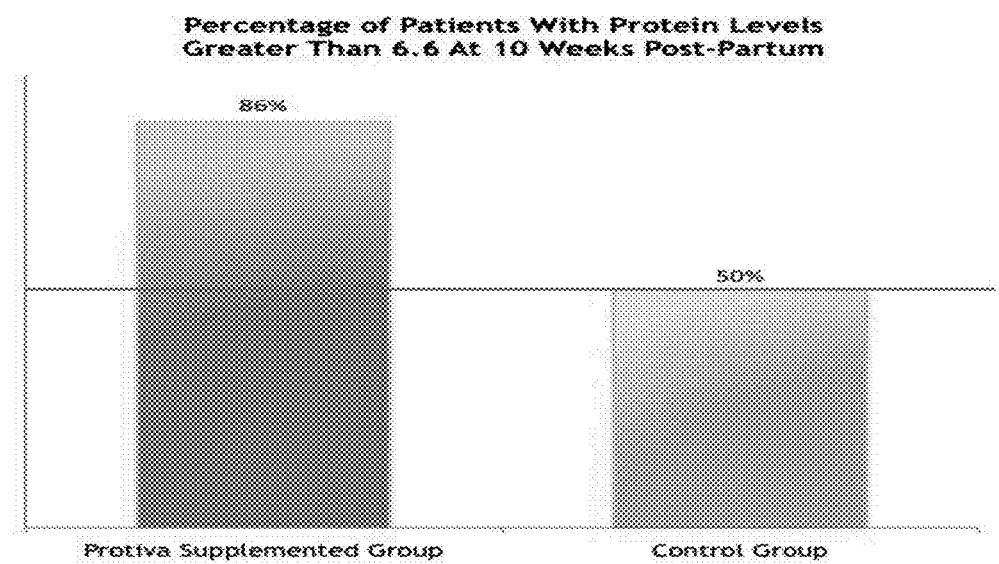

Here, the safety results were that the PROTIVA™ products were well tolerated. There were no serious adverse events reported during the study. Further, one hundred percent (100%) of the control patients presented with an initial blood protein level below the mean pregnancy average of 6.6 (g/dL), and 27% had an initial blood protein level below 6.0 (g/dL). Ninety-Five percent (95%) of the study patients that took PROTIVA™, had an initial blood protein level below the mean pregnancy average of 6.6 (g/dL) and 33% had an initial blood protein level below 6.0 (g/dL). At six weeks post-delivery, 94% of the patients taking PROTIVA™ improved their blood protein levels above the mean pregnancy average of 6.6 (g/dL). This compares to 64% of the control group who improved blood protein levels above the mean pregnancy average of 6.6 (g/dL), as shown in FIG. 4A. At ten weeks post-delivery, 86% of study patients who took PROTIVA™ maintained their blood protein levels above the mean of 6.6 (g/dL). This compares to only 50% of the control group, as shown in FIG. 4B.

Here, the clinical study looked to address a way to determine the underlying protein status in a group of healthy women from a community where food and protein resources are abundant, and then determine if protein supplementation would have an impact on the measurement parameters and pregnancy outcomes. What we found with respect to underlying protein and albumin levels was very interesting. The fact that the great majority of patients had serum levels below the normal median and even completely below the normal range was not necessarily new. It was surprising that in an affluent area with nutritional abundance that such a high percentage would fall into this low range. With collagen protein supplementation we were able to demonstrate a 94-100% improvement in protein levels in study patients. The control patients showed a much lower improvement even with dietary advice and overall the protein group showed a 72% improvement over control patients. Further, the study also showed an improvement in overall quality of life scores and wound healing indices as measured by the WHOQOL-BREF and REEDA pre and post study evaluations. Patients who entered the study were apparently healthy and without underlying depressive disorders, and it was not anticipated that they would have such dramatic improvement in both of these outcomes.

It is contemplated within the scope of the disclosure described herein that any other type or one or more of natural medicinal, nutritional, nutraceutical, mineral, and/or herbal composition, ingredient, extracts, or oils may be added or incorporated into the one or more formulations of the disclosure described herein.

Since many possible embodiments may be made of the invention without departing from the scope thereof, it is to be understood that all matters herein set forth or shown in the accompanying drawings are to be interpreted as illustrative, and not in a limiting sense. While specific embodiments have been shown and discussed, various modifications may of course be made, and the disclosure described herein is not limited to the specific forms or arrangement of parts or method of assembly described herein, except insofar as such limitations are included in the following claims. Further, it will be understood that certain features and sub-combinations are of utility and may be employed without reference to other features and sub-combinations.

What is claimed is:

1. A nutritional protein supplement formulation, comprised of:
    hydrolyzed collagen protein comprising more than 50% wt. of the formulation;
    Rebaudioside-A (Reb-A);
    vitamin C;
    copper acid chelate; and
    a flavoring ingredient.

2. The formulation of claim 1, wherein the hydrolyzed collagen protein is comprised of about 57% wt. of the formulation.

3. The formulation of claim 1, wherein the hydrolyzed collagen protein is comprised of bovine or porcine animal protein sources.

4. The formulation of claim 1, further comprising L-Isoleucine, L-Leucine, and L-Valine.

5. The formulation of claim 1, further comprising vitamin A, vitamin E, and vitamin D3.

6. The formulation of claim 1, further comprising potassium citrate.

7. The formulation of claim 1, further comprising zinc.

8. The formulation of claim 1, further comprising calcium.

9. A nutritional protein supplement formulation, comprised of:
- hydrolyzed pork collagen protein comprising about 57% wt. of the formulation;
- Rebaudioside-A (Reb-A);
- vitamin C;
- copper acid chelate;
- L-Isoleucine comprising less than 1% wt. of the formulation;
- L-Leucine comprising less than 1% wt. of the formulation;
- L-Valine comprising less than 1% wt. of the formulation; and
- a flavoring ingredient.

10. The formulation of claim 9, further comprising vitamin A, vitamin E, and vitamin D3.

11. The formulation of claim 9, further comprising vitamin A, vitamin E, and vitamin D3.

12. The formulation of claim 9, further comprising potassium citrate.

13. The formulation of claim 9, further comprising zinc.

14. The formulation of claim 9, further comprising calcium.

* * * * *